(12) United States Patent
Hagen et al.

(10) Patent No.: US 11,779,287 B2
(45) Date of Patent: Oct. 10, 2023

(54) COMPUTED TOMOGRAPHY IMAGING

(71) Applicant: UCL Business Ltd, London (GB)

(72) Inventors: Charlotte Hagen, London (GB); Fabio Alessio Vittoria, London (GB); Marco Endrizzi, London (GB); Alessandro Olivo, New Barnet (GB)

(73) Assignee: UCL Business Ltd, London (GB)

( * ) Notice: Subject to any disclaimer, the term of this patent is extended or adjusted under 35 U.S.C. 154(b) by 304 days.

(21) Appl. No.: 17/298,874

(22) PCT Filed: Dec. 12, 2019

(86) PCT No.: PCT/EP2019/084964
§ 371 (c)(1),
(2) Date: Jun. 1, 2021

(87) PCT Pub. No.: WO2020/120705
PCT Pub. Date: Jun. 18, 2020

(65) Prior Publication Data
US 2022/0015720 A1 Jan. 20, 2022

(30) Foreign Application Priority Data
Dec. 13, 2018 (GB) ..................... 1820362

(51) Int. Cl.
*A61B 6/03* (2006.01)
*A61B 6/00* (2006.01)
(Continued)

(52) U.S. Cl.
CPC .............. *A61B 6/027* (2013.01); *A61B 6/032* (2013.01); *A61B 6/4064* (2013.01);
(Continued)

(58) Field of Classification Search
CPC ....... A61B 6/027; A61B 6/032; A61B 6/4064; A61B 6/5205; A61B 6/542; A61B 6/06;
(Continued)

(56) References Cited

U.S. PATENT DOCUMENTS

| 2015/0049860 A1* | 2/2015 | Das ..................... A61B 6/4035 |
| | | 378/62 |
| 2016/0199019 A1 | 7/2016 | Ruimi et al. |
| 2018/0042561 A1 | 2/2018 | Sjolin et al. |

FOREIGN PATENT DOCUMENTS

| WO | 2013011317 A1 | 1/2013 |
| WO | 2014202949 A1 | 12/2014 |

OTHER PUBLICATIONS

GB 1820362.0; Search Report; dated Jun. 7, 2019; 3 pages.
(Continued)

*Primary Examiner* — Courtney D Thomas
(74) *Attorney, Agent, or Firm* — Kilpatrick Townsend & Stockton LLP

(57) ABSTRACT

A computed tomography method seeking higher resolutions without imposing a dose increase is described. A mask (10) forms a plurality of X-ray beam lets (14) which are passed through a subject (6), and images are captured on X-ray detector (8). The subject (6) is moved with respect to the X-ray detector and mask, including a rotation around a y axis, and a computed tomography image is reconstructed from the plurality of measured datapoints. The beam lets (14) are of small size. FIGS. 4-8 are blurred, FIGS. 10, 11 and 16*b* contain too small letters/numbers.

20 Claims, 12 Drawing Sheets

(51) Int. Cl.
  *A61B 6/02* (2006.01)
  *A61B 6/06* (2006.01)
(52) U.S. Cl.
  CPC ............ *A61B 6/5205* (2013.01); *A61B 6/542* (2013.01); *A61B 6/06* (2013.01); *A61B 6/4291* (2013.01); *A61B 6/484* (2013.01)
(58) Field of Classification Search
  CPC ..... A61B 6/4291; A61B 6/484; A61B 6/4035; G06T 11/003
  See application file for complete search history.

(56) References Cited

OTHER PUBLICATIONS

PCT/EP2019/084964; International Search Report and Written Opinion; dated Mar. 13, 2020; 16 pages.

Hagen, Charlotte K.; "Theoretical Framework for Spatial Resolution in Edge-Illumination X-Ray Tomography;" Physical Review Applied, vol. 10, No. 5; Nov. 21, 2018; 11 pages.

* cited by examiner

COMPUTED TOMOGRAPHY IMAGING

The invention relates to a method of computed tomography (CT) imaging and apparatus for carrying out CT imaging.

BACKGROUND

X-Ray CT has become a very important technique for diagnostic imaging, especially in the field of medicine. However, the technique does involve exposing the subject to ionising X-ray radiation. The technique generally results in lower resolution than conventional two dimensional X-ray imaging, such as mammography or standard X-ray imaging. The reason for the lower resolutions achieved is that to increase an image resolution in two dimensions there is normally a quadratic increase in dose—so to double the resolution the dose must be multiplied by 4. An increase in resolution in three dimensions leads to a cubic increase in dose. Therefore, to keep doses to reasonable levels lower resolutions are used than for conventional two dimensional X-ray imaging which has significant implications for what CT can and cannot detect and resolve. This in turn can have an effect on the sensitivity of CT and its ability to detect lesions.

There is accordingly much interest in reducing the dose in CT.

One way of doing this is to reduce the X-ray tube current or the exposure time per view to simply reduce the dose used. However, there remains a need to collect enough photons to reliably reconstruct the CT image from the images taken.

Another approach is sparse-view CT which takes projections at sparse view angles, i.e. only a limited numbers of angles.

One proposal is made by Lee et al, "Moving Beam-Blocker-Based Low-Dose Cone-Beam CT", IEEE transactions on nuclear science, Volume 63, number 5, October 2016. In this approach, which has been referred to as many-view undersampling, MVUS, a beam blocker is placed between the X-ray source and the patient, the beam blocker having multiple opaque strips. This reduces the dose. The paper proposes an image reconstruction algorithm.

In spite of these advances, there remains a need for capturing high resolution CT images. In some applications, there is also a need for low doses.

SUMMARY OF THE INVENTION

According to a first aspect of the invention there is provided a computed tomography method, comprising:
  generating an X-ray beam travelling in a beam direction z from an X-ray source having a focal spot;
  using a mask having a plurality of block regions and a plurality of apertures having a period p in a first orthogonal direction x orthogonal to the beam direction to divide the beam into a plurality of X-ray beamlets;
  passing the X-ray beam through a subject;
  capturing an image on an X-ray detector having an array of pixels extending in the x direction, the plurality of pixels having a period a in the x direction;
  moving the subject with respect to an imaging system comprising the X-ray source, mask and the X-ray detector;
  capturing a plurality of images as the subject is moved with respect to the imaging system, each image corresponding to a rotation angle $\theta$ and being in the form of a plurality of measured datapoints as a function of x, and storing the measured datapoints; and
  reconstructing a computed tomography image from the plurality of measured datapoints;
  wherein the mask is structured such that each of the beamlets defines a region in the subject which when geometrically scaled to the detector mask is less than F, wherein F is the full width half maximum FWHM of the overall spread function caused by the combination of finite size of the focal spot and the finite pixel resolution at the plane of the detector, in the x-direction; and
  the step of reconstructing reconstructs the three-dimensional computed tomography image at a finer pitch than the period p of the mask.

Compared with the method proposed in Lee et al, the method according to the present invention has a much finer grained array of beamlets, smaller than F (as defined in claim 1). This finely grained measurement results in the sinogram array having a set of measured datapoints resulting in good high definition images.

The invention is able to provide an improved resolution by blocking some of the X-rays in such a way that each of the beamlets probes a smaller region of the subject than would be determined by the parameter F. Because the size of the beamlets provides a limitation on the area of the subject probed by each of the beamlets, the data captured provides information at a smaller length scale than would normally be determined by F, and at a smaller length scale than the period of the mask. This additional information from images captured at a number of rotation angles may be combined to provide a better resolution than would otherwise be possible. This requires that the reconstruction method takes account of the data captured in this way—a variety of approaches to reconstruction are discussed below.

If this method is compared with the method proposed in the prior art document discussed above, Lee et al, we note that in Lee et al the beam blockers of the mask correspond to a size greater than one pixel (typically 6 to 18 pixels) and so this improved resolution is not achieved.

The proposed method also does not capture data for all potential datapoints at the fine length scale corresponding to the widths of the individual beamlets at the sample, so seen at that finer length scale there are additional, non-measured datapoints between the measured datapoints. Conveniently, the measured datapoints may be stored in a sinogram array as a function of $\theta$, x and y. The array may also contain elements corresponding to additional non-measured values, corresponding to locations in the samples that are blocked by the mask. The additional non-measured datapoints can be dealt with at the stage of reconstruction, either by interpolation of missing datapoints in the sinogram array, or by using a reconstruction algorithm that is adapted to the presence of the missing datapoints, for example an iterative algorithm. This will be described in more detail below.

For example, in the x direction, the density of measured datapoints may be the density of pixels (or less), whilst the density of elements in the sinogram array may be at least double the density of pixels whereby the step of storing the measured datapoints in the sinogram array leaves at least half the datapoints as the additional non-measured datapoints.

In a particularly preferred embodiment the mask is on the X-ray source side of the subject in the beam direction z so that the X-ray beamlets pass through the subject. In this way, the high resolution is achieved in combination with a low dose, as the X-rays absorbed by the mask do not pass through the subject. This ability to combine high resolution with low dose is particularly important in imaging living subjects where minimising X-ray dose is a key goal.

In a preferred embodiment, each beamlet corresponds to a respective pixel, i.e. the mask is structured such that there is one beamlet in the x direction incident on each pixel. The beamlets may thus be smaller than the size of the pixel, i.e. do not cover the full surface of the pixel. For example, each beamlet may only correspond to a region (in the x direction) of for example one eighth to one quarter of the size of the pixel. It is the small size of these beamlets that allows the capture of fine structure in the subject on a smaller scale than the size of the pixel.

Where a region of the subject is said to "correspond" to one pixel, what is meant is the beamlet samples only a region of the subject, and that region, when geometrically scaled to the detector plane, is contained within the size of one pixel. In an arrangement in which the beamlets spread, the resolution at the subject will be higher resolution than the size of the pixel as there will be effective magnification between subject and detector, for example in the range 1.2 to 3.

In a particular arrangement, to arrange for each measured datapoint to correspond to a respective beamlet, each beamlet may be incident on a single respective pixel in the first orthogonal direction by arranging the period of the apertures p and the pixel a such that p=a/m, where m is the effective magnification between the mask and the detector.

The step of moving the subject with respect to the imaging system may comprise moving by rotating around an axis in the second orthogonal direction y, and translating in the first orthogonal direction x, typically by small amounts of the order of the pixel and typically smaller, for every rotational increment. This motion pattern results in a useful set of measured datapoints for improved image reconstruction, that may be referred to as a rototranslational motion. In embodiments, only a small translation in the first orthogonal direction is provided between adjacent measurements at different angles, for example in the range corresponding to 0.2 to 0.5 pixels. Such a motion pattern is referred to as a "rototranslational" pattern but it should be noted that the motion is not necessarily continuous, and case measurements are taken only at specific points along the rototranslational motion.

In order to carry out conventional CT image reconstruction to generate the three dimensional image, the fact there are missing, non-measured datapoints need to be dealt with by one means or another.

In one approach, non-measured datapoints in the sinogram array are calculated by interpolation. After the non-measured datapoints are calculated, any conventional image reconstruction algorithm may be used for generating the computed tomography image from the sinogram array, for example a filtered backprojection. This approach requires less computing power than alternative approaches, in particular less computing power than an iterative reconstruction approach set out below.

Accordingly, the step of reconstructing a computed tomography image may comprise carrying out an interpolating step to obtain values of the sinogram array for non-measured datapoints. There is a particular benefit in using a rototranslational motion when carrying out interpolation, as the rototranslational motion allows an improved spread of measured datapoints across the sinogram array leading to improved interpolation.

In a particularly preferred arrangement, the interpolating step may use a 2D cubic interpolation scheme.

The sinogram array may have a plurality of rotation angles separated by $\Delta\theta$ and a plurality of values x for a particular rotation angle $\theta$ separated by $\Delta x$. The translation of the subject between adjacent rotation angles separated by $\Delta\theta$ may corresponds to an integer number of array elements, i.e. to $n\Delta x$. Although in some embodiments n may be an integer, it is also possible for n to be any real number. The integer n may be selected to maximise a grid quality indicator describing how closely the grid of measured datapoints in the sinogram array resembles a hexagonal grid.

As an alternative to interpolating to find the missing datapoints, the reconstruction algorithm can directly process only the measured datapoints. In this case, it is not possible to use traditional types of reconstruction algorithm as these generally require a full set of datapoints at the required resolution. As an alternative, a computed tomography image may be reconstructed directly from the measured data points using an iterative reconstruction method. This approach has the advantage that it removes the need for an interpolation step which could potentially blur the resulting image.

The skilled person will note that a translation of the subject with respect to the imaging system in the first orthogonal direction corresponds to a translation in a different direction to that used in helical CT, in which the axis of rotation and direction of translation are parallel. However, the method of the invention is completely compatible with the use of helical CT and accordingly the method may comprise capturing data in a helical pattern by translating the subject with respect to the detector and mask additionally in the second orthogonal direction y.

The mask may be structured to provide a two-dimensional array of beamlets in the x and y directions. Such a mask should be used with capturing data in a helical pattern and may improve the resolution also along Y as well as X and Z.

The method proposed above is also very easy to combine with phase contrast imaging. The captured images may accordingly be phase contrast images.

These images may be obtained in a variety of ways. For example, the method may comprise providing a detector mask in front of the X-ray detector, the detector mask comprising a plurality of apertures spaced apart in the first orthogonal direction and each beamlet overlapping one edge of a respective aperture in the first orthogonal direction. Alternatively to the use of a detector mask, the beamlets may be aligned with the area separating adjacent pixels between the pixels of the detector with each beamlet overlapping one edge of the pixel separator in the first orthogonal direction. In this case, the pixel separators act as an equivalent to the detector mask. Alternatively, the density of pixels in the x direction may be higher than the density of beamlets so that individual beamlets can be resolved.

According to another aspect of the invention there is provided a computed tomography method, comprising:
generating an X-ray beam travelling in a beam direction z from an X-ray source having a focal spot;
using a mask having a plurality of block regions and a plurality of apertures having a period p in a first orthogonal direction x orthogonal to the beam direction to divide the beam into a plurality of X-ray beamlets;
passing the X-ray beam through a subject;
capturing an image on an X-ray detector having an array of pixels extending in the x direction, the plurality of pixels having a period a in the x direction;
moving the subject with respect to an imaging system comprising the X-ray source and the X-ray detector, including a rotation by a rotation angle $\theta$ around an axis extending in a second orthogonal direction y orthogonal to the beam direction z;

capturing a plurality of images as the subject is moved with respect to the imaging system, each image corresponding to a rotation angle θ and being in the form of a plurality of measured datapoints as a function of x, and storing the measured datapoints; and reconstructing a computed tomography image from the plurality of measured datapoints;

wherein the step of moving the subject with respect to mask and detector comprises moving the subject by rotating the subject around an axis in the second orthogonal direction y, and translating the subject in the first orthogonal direction x.

By moving the subject in a rototranslational motion the set of measured datapoints captured for different angles covers the three dimensional space of θ, x and y more efficiently in the sense that the distance of the unmeasured datapoints to a measured datapoint in the three dimensional space is typically less than by simple rotation of the subject.

This aspect may be combined with the optional features indicated in the previous paragraphs.

In another aspect, the invention relates to a computed tomography apparatus, comprising:

an X-ray source for generating a beam travelling in a beam direction z from a focal spot;

a mask spaced from the X-ray source along the beam direction having a plurality of block regions and a plurality of apertures having a period p in a first orthogonal direction x orthogonal to the beam direction z for dividing the beam into a plurality of X-ray beamlets;

a stage for supporting a subject in the beam;

a detector having an array of pixels having a period a in the x direction for capturing an image on an X-ray detector;

a drive for moving the stage with respect to an imaging system comprising the X-ray source, mask and the X-ray detector; and a computer control means for controlling the drive to move the stage with respect to the mask and the detector and for capturing a plurality of images on the detector;

wherein the mask is structured such that each of the beamlets defines a region in the subject which when geometrically scaled to the detector mask is less than F, wherein F is the full width half maximum FWHM of the overall spread function caused by the combination of finite size of the focal spot and the finite pixel resolution at the plane of the detector, in the x-direction.

The apparatus may further comprise a computer analysis means for reconstructing a computed tomography image from the plurality of images at a finer pitch than the period p of the mask, wherein the computer control means is arranged to control the computed tomography apparatus to carry out a method as set out above.

BRIEF DESCRIPTION OF DRAWINGS

For a better understanding of the invention embodiments will now be described, purely by way of example, with reference to the accompanying Figures, in which:

FIGS. 16 (b) to (d) show CT images obtained from experimental data.

Figure 1:
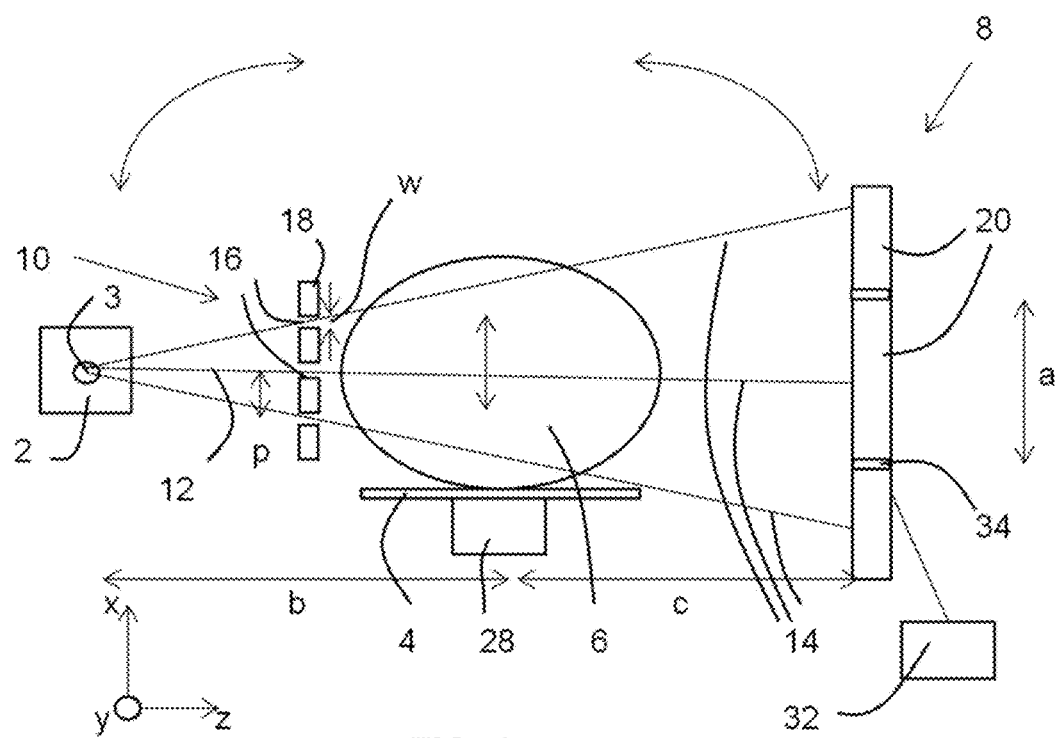
FIG. 1 shows apparatus according to an embodiment of the invention.

The drawings are schematic and not to scale.

DETAILED DESCRIPTION

The CT apparatus comprises an X-ray source 2 having a focal spot 3, a subject stage 4 for supporting a subject 6 such as a human being or a tissue sample, and an X-ray detector 8 in the form of a two dimensional pixel detector having a plurality of pixels 20 of pixel size a. The subject stage is not fixed in position as will be described in more detail below. Individual pixels 20 are separated by regions 34.

A mask 10 is provided having a plurality of apertures 16 of width w at a mask period p, the apertures being between block regions 18 in the form of septa. The beam 12 emitted by the X-ray source 2 is broken up into a plurality of beamlets 14 by the mask 10, each beamlet being generated by a respective aperture 16. The mask period p matches the detector pixel size a in that p=a/m where m is the magnification between mask and detector. In other words, each pixel 20 receives a respective beamlet 14.

A processing apparatus 32 is connected to the X-ray detector 8 for processing the captured images. The processing apparatus may also be connected to other elements to control them, for example the X-ray source 2 and drive 28. The processing apparatus 32 carries out image reconstruction to create a 3D representation of the subject 6 as will be described in some detail below. Thus, in this arrangement the processing apparatus functions both as a control computer and as an image analysis computer. Alternatively, separate computers may be provided to carry out these functions.

In this arrangement, an image of a subject at the detector 8 includes information at additional spatial frequencies beyond the cut-off normally imposed by source and detector. To a first approximation, spatial frequencies up to the inverse of the aperture width, i.e. up to 1/w, are transferred. It will be appreciated that the presence of higher spatial frequencies allows better resolution.

Depending on the ratio p/w, typically in the range 3 to 8, these frequencies are significantly higher than those in a conventional CT scanner with the same size of pixels, x-ray focal spot and relative position of the subject with respect to x-ray source and detector. There is thus additional information in the detected image. Simultaneously, the absorbing septa 18 between the apertures 16 absorb significant amounts of X-rays lowering the dose.

This example is an example of undersampling the data to reduce the dose. In order to make use of the undersampled data, the missing information needs to be replaced or compensated for one way or another. Two example ways of processing the data are discussed below—in the first missing data that is not captured because the mask 10 shields the relevant part of the subject is first interpolated before a conventional CT reconstruction algorithm is used. In the second, an adapted image reconstruction algorithm using iteration is used to directly reconstruct the 3D image from the captured datapoints.

FIG. 1 illustrates schematically the arrangement of beam 12, subject 6, mask 10 and detector 8. Note that the direction from left to right will be referred to as the beam direction, or the z axis; the direction in the plane of the paper orthogonal to the beam direction will be referred to as the first orthogonal direction or the x direction, and the direction orthogonal to the paper will be referred to as the second orthogonal direction or the y direction.

In this regard, note although the mask 10 in the present application is used for the purposes of increasing resolution for a given dose, or alternatively for reducing the dose for a given resolution, the position of this mask 10 is entirely compatible with the mask position proposed in WO2014/202949 for the purposes of phase contrast imaging.

Figure 2:
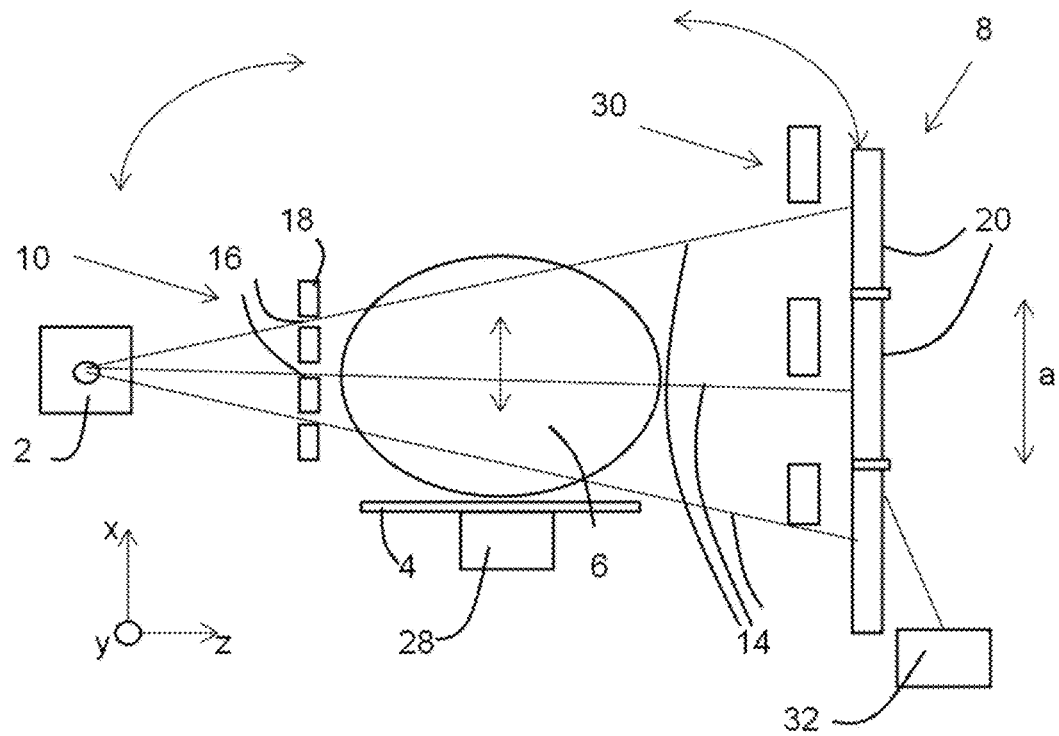
FIG. 2 shows apparatus according to an alternative embodiment of the invention.

It is therefore straightforward to adapt the apparatus to switch between conventional and phase contrast modes simply by providing additionally detector mask 30 in the phase contrast case. FIG. 2 illustrates this alternative arrangement, in this case adapted for carrying out phase contrast imaging. A further set of beam stops is provided in front of the detector in the form of detector mask 30 having apertures corresponding to respective pixels. In this case, the phase contrast imaging can take place in the manner proposed in WO2014/202949.

Alternatively, the beamlets may be aligned with the separation line between adjacent pixels in the detector. In a further alternative embodiment, a high resolution detector is used, sufficient to resolve the beamlets directly without requiring a detector mask 30.

During a specific measurement the subject is moved with respect to the source 2, mask 10 and detector 8 which are held in a fixed relationship and make up an imaging system 2,8,10. This provides the plurality of 2D images needed to carry out the reconstruction of the 3D image. Those skilled in the art will realise that the source 2, mask 10 and detector 8 may be held fixed and the subject 6 moved, or alternatively the subject 6 may be held fixed and the imaging system 2, 8,10 moved with respect to the subject. This applies both to the rotation and to the translation(s) where present.

In a particularly preferred embodiment the motion of subject with respect to the source, mask and detector combines a rotary motion around an axis extending in the y direction and a translation in the x direction with respect to the axis. These motions are illustrated by the arrows in FIGS. 1 and 2 and results in a rototranslational motion schematically illustrated in FIG. 3. The reasons why this may provide an improved resolution will now be discussed with reference to some theoretical considerations.

Theory

Firstly, let us consider how data at a smaller feature size, equivalent to higher frequencies may be present in the captured data at all. Consider the case that the mask is removed from an arrangement according to the invention. In this case, the resolution of each image is given by a spread function obtained by combining the broadening effects caused by the detector pixel and the focal spot having a width F, which may be conveniently defined as a full width at half maximum (FWHM). This resolution is largely determined by the finite size of the beam spot 3 at the X-ray source and the finite area to which each pixel 20 responds.

More mathematically, to cope with the fact that the focal spot and detector are not in the same plane it is necessary to map the effect of the finite size $F_{fs}$ of the focal spot onto the detector plane. This is done by assuming a nominal pinhole at the subject, at a distance b from the beam spot and c from the detector, the finite size of the beam spot projected onto the detector is then $F_{fs}(c/b)$. For the avoidance of doubt, the pinhole is simply a mathematical construct to calculate the effect of the finite beam spot size on the resulting measurement. The finite size of the pixel detector $F_{pd}$ is caused by the finite size of the pixel and any cross-talk between adjacent pixels. There is no need for correction by any magnification factor as this is already measured at the detector plane. The total effect of both of these together to form the detector pixel point spread width F at the detector plane is then typically given by a quadrature sum:

$$F = \sqrt{(F_{pd})^2 + \left(\left(\frac{c}{b}\right)F_{fs}\right)^2}.$$

Thus, F will not be less than the size of one pixel and typically larger depending on the size of the beam spot at the X-ray source. This limit on the resolution in each captured image limits the resolution of the calculated CT image.

In order to improve the resolution beyond this usual limit the invention proposes the use of a mask 10 which creates beamlets which correspond to less than the point spread width F mapped onto the detector plane. Thus, taking the beamlet size at the subject to be a width s, s should be less than F when geometrically scaled onto the detector plane so taking the same distances b and c as in the previous paragraph s((c+b)/b)<F. As long as the inequality is satisfied, some improvement may be achieved but in general terms the inventors have found that values of s((c+b)/b) between one 0.1 F and 0.5 F, especially 0.12 F to 0.25 F are suitable, i.e. typically the beamlets probe an eighth or a quarter of the sample.

Figure 4:
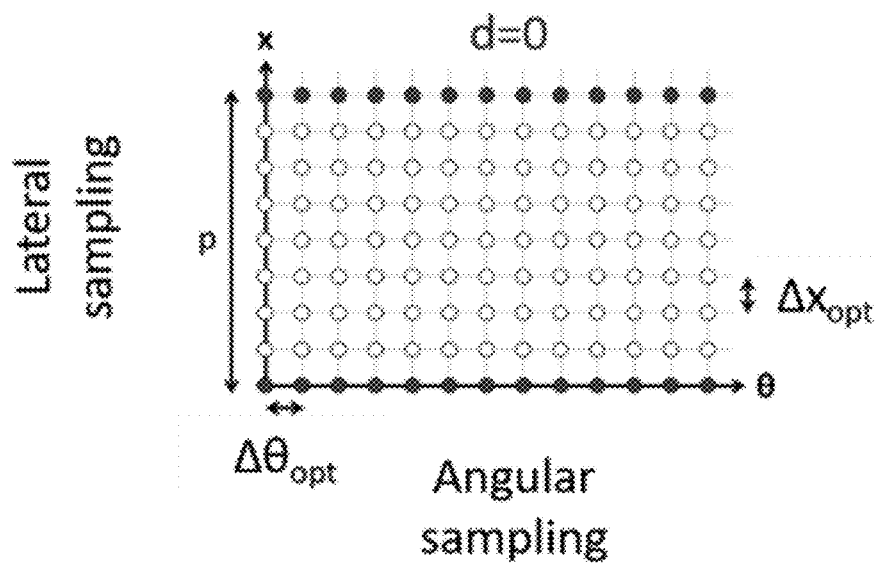
FIGS. 4 to 8 illustrates the sampled points (full circle) and additional points (open circle) according to various embodiments.

Referring to FIG. 4, a grid of points is shown which will be referred to as a sinogram. The sinogram represents a two-dimensional image of a number of pixels extending in the x and y directions for each of a number of rotation angles θ. The sinogram thus represents a three dimensional abstract space indexed by (θ, x, y). In FIG. 4, the y direction is into the paper and not shown. In the present example the mask 10 comprises slits extending in the y direction, i.e. without additional structure in the y direction, and the detector 8 is a two dimensional detector which samples the image in both the x and y directions. The mask may in alternative embodiments have structure in the y direction as well as will be discussed below.

In the event of a full sampling carried out at a high resolution corresponding to that smaller length scale, a lateral sampling of the sample could occur at an interval Δx in the x direction. This is represented by the leftmost column of points, both filled circles and open circles, at a constant angle θ. Each column of points to the right represents an image captured at a different rotation angle θ. To capture this array of points, after each image has been captured, the sample 6 is rotated with respect to mask 10 and detector 8 by an angle Δθ and the next image captured which delivers the next row of sampling points. This is repeated for a number of different angles θ.

Such a full sampling could be carried out without a mask 10 but in a different configuration, i.e. with a system using a proportionally higher resolution obtained by using a detector with a smaller pixel possibly combined with a smaller x-ray focal spot. However, a different approach is used to capture high resolution high dose images for comparison with those made using a method according to embodiments of the invention. This approach will be known as dithering, and is carried out in apparatus containing the mask by moving the sample, or equivalently the imaging system, to a number of different positions. In the case where the beamlets only capture an eighth of the subject, it is necessary to repeat the measurement eight different times with different mask positions to cover the entire sample.

FIG. 4 illustrates the case according to an embodiment of the invention that a single image is captured at each rotation angle θ. The use of the narrow beamlets mean that although the method can capture data corresponding to a smaller length scale, the data is only captured for a subset of possible values of x corresponding to the values of x indicated with filled circles. The values of x indicated with open circles relate to positions of the subject for which the x-rays are blocked by the mask and accordingly for which data is not collected.

In the arrangement shown in FIG. 4, the subject is simply rotated between each captured image, resulting in the same positions x being sampled for each different angle θ as represented by the horizontal rows of filled circles at the same value x for each different angle.

Figure 5:
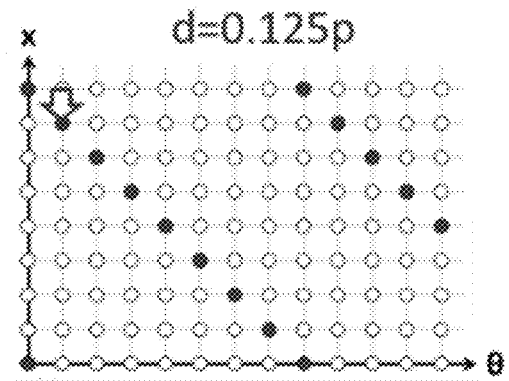
Figure 7:
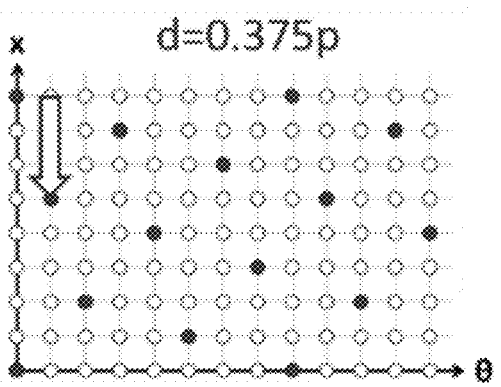
Figure 8:
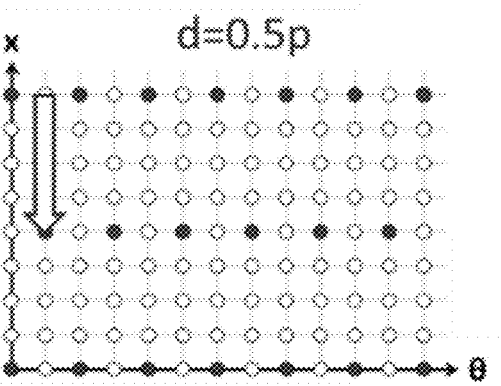

In a further development, as well as rotating the subject after capturing one image at a specific angle θ, the subject is moved in the x direction slightly with respect to the mask and detector before capturing the next image at the angle θ+Δθ. This corresponds to the arrangements illustrated in FIGS. 5, 6, 7 and 8. In these cases, the grid is displaced by a distance d in the x direction between each measurement, where d is a different fraction of the period of the mask p in each case—in FIG. 5 the displacement d in the x direction corresponds to 0.125p, in FIG. 6 to 0.25p, in FIG. 7 to 0.375p and in FIG. 8 to 0.5p. In each case different points (shown as filled circles) of the sinogram grid are sampled. Such a combination of rotation and displacement will be referred to as rototranslational sampling as the subject moves in a rototranslational path being both rotated and translated.

Thus, FIGS. 4 to 8 show the sinogram sampling grid as a function of the distance (d) by which the sample is laterally displaced per rotational increment (Δθ), where d=0 in FIG. 4. The empty circles represent the "optimal" grid (i.e. the one which would preserve spatial frequencies up to 1/w), in which data are sampled with lateral and angular intervals of $\Delta x_{opt}=w/2$ and $\Delta \theta_{opt}=1/(2+t/w)$. The lateral sampling interval is now defined by the mask period (p), causing the abovementioned under-sampling along this direction since $p > \Delta x_{opt}$. Without rototranslational sampling, i.e. if no lateral translation of the sample is carried out simultaneously with the rotation (d=0, FIG. 4), the available datapoints are densely packed along the angular axis, but spaced far apart along the lateral axis. In other words, the lateral and angular sampling intervals are unbalanced, which is suboptimal for data recovery methods. With rototranslational sampling, as the value of d is increased (FIGS. 5 to 8), this unbalanced distribution gets broken up and the available data are spread more evenly across the sinogram. For values of d at which the interpolation distances are roughly comparable along all directions, this leads to a better performance of 2D interpolation schemes.

Without wishing to be bound by theory, we present here a quantitative analysis of the performance of the rototranslational scheme as a function of the sample translation distance d. We start by noting that, if dose increase is to be avoided, we are limited to the acquisition of a fixed number of datapoints (M, which is the product of the number of angular projections and the number of beamlets irradiating the sample). It may be assumed that the best scenario is an arrangement of the sampled data on a hexagonal grid (including the hexagons' centre points), as in this way the interpolation distances between any two adjacent datapoints are the same. This ideal, uniform interpolation distance ($f_{hex}$) can be calculated via simple geometrical principles. As visualised in FIG. 4(a), $f_{hex}$ is the side length of an equilateral triangle with area B, hence $$f_{hex} = \sqrt{\frac{4}{\sqrt{3}}B}.$$

In turn, B=A/2, with A being the area of the "Brillouin zone" of the hexagonal grid; therefore:

$$f_{hex} = \sqrt{\frac{2}{\sqrt{3}}A}.$$

The area A can be expressed as the M'th fraction of the sampled region of sinogram space; however, as the lateral and angular axes of the sinogram are not of comparable dimensions (their units are m and rad), it is necessary to express A relative to the optimal lateral and angular sampling intervals $\Delta x_{opt}$ and $\Delta \theta_{opt}$. That is, $$A = \frac{t\pi}{\Delta x_{opt} \Delta \theta_{opt} M},$$

where t is the sample thickness and π is the total range for the sample rotation; therefore:

$$f_{hex} = \sqrt{\frac{2}{\sqrt{3}} \frac{t\pi}{\Delta x_{opt} \Delta \theta_{opt} M}}.$$

Next, we can analyse the sampling grids obtained for different values of d, and establish a measure for the "closeness" of each of them to the ideal, hexagonal arrangement. Each grid can be described by the pair of vectors $a_1=(\Delta\theta_{opt},-d)$ and $a_2=(\Delta\theta_{opt},p-d)$, that is, every grid point $a_{ij}$ can be expressed as the linear combination: $a_{ij}=ia_1+ja_2$, where i and j are integers chosen such that $a_{ij}$ is contained within the sampled sinogram region ([−π/2, π/2)×[−t/2, t/2]). This leads to the following equation for the minimal distance between any two adjacent datapoints:

$$f_{p,w}(d) = \min_{(i,j),i+j\neq 0}\left(\sqrt{(i+j)^2 + \left(\frac{ip+(i+j)d}{\Delta x_{opt}}\right)^2}\right) \quad (1)$$

Note that we again have applied the normalisation by $\Delta x_{opt}$ and $\Delta\theta_{opt}$ to ensure that lateral and angular dimensions are comparable. Equation (1) enables us to define a grid quality indicator, describing how closely any grid described by $a_1$ and $a_2$ resembles a hexagonal arrangement:

$$g_{p,w}(d) = 1 - \frac{|f_{p,w}(d) - f_{hex}|}{f_{hex}} \quad (2)$$

Figure 9:
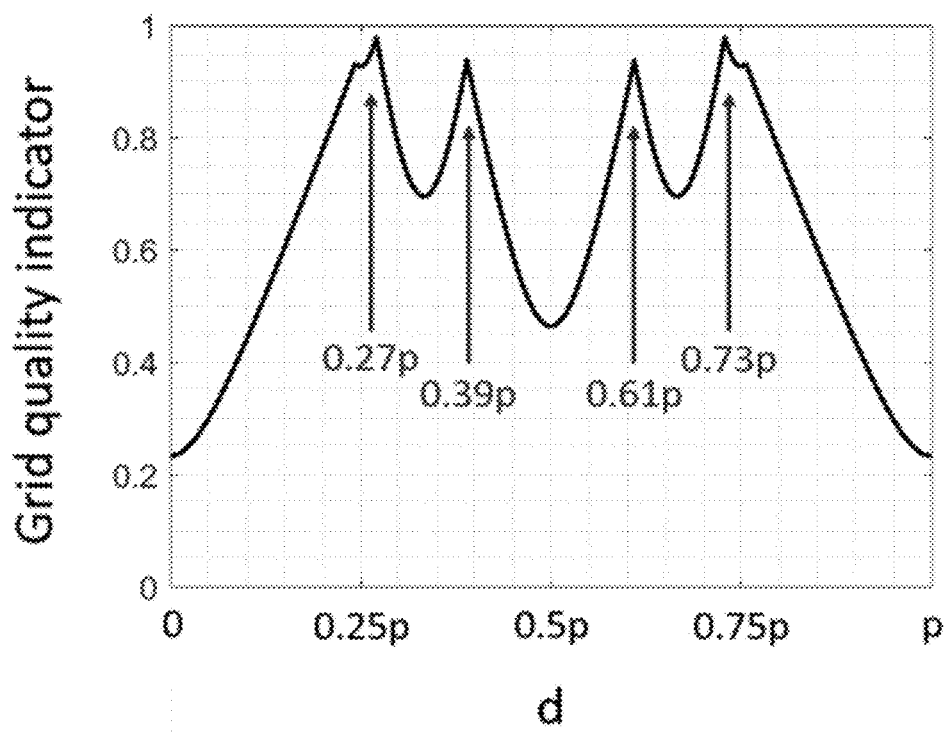
FIG. 9 illustrates a quality measure as a function of the displacement d.

This is plotted as a function of d in FIG. 9, assuming a mask period and aperture width of p=80 µm and w=10 µm. Note that it is sufficient to consider d within the range [0,p), as the effect of the rototranslational scheme repeats itself for values outside of this range. In FIG. 9, the value 1 represents a hexagonal arrangement, and the closer the curve to this value the better the performance of the corresponding grid. As can be seen, the unbalanced grid obtained without rototranslational sampling (d=0, FIG. 4) indeed performs worst under this metric. On the contrary, since the curve has well-defined local maxima at d=0.27p, d=0.39p, d=0.61p and d=0.73p, a virtually hexagonal arrangement can be achieved with rototranslational sampling when carefully selecting d. This is in line with the schematic in FIG. 7, where the grid shown for d=0.375p (panel (d)) closely resembles a hexagonal one. Note that the grid quality indicator changes for different combinations of p and w; thus, it is important that a new, dedicated value for d is selected whenever these parameters are changed.

Note that the translation between adjacent images in the x direction is small, smaller than the size of the pixel as typically d is less than 1p. Moreover, the effect of the movement is essentially cyclical. Taking appropriately into account geometric scaling due to magnification, movement by a number of pixels greater than 1 effectively corresponds to the movement by the fractional part only of the size of the movement. For example, movement by 1.5 pixels is essentially equivalent to movement by 0.5 pixels. There is no need to allow for motions over distances corresponding to multiple pixels. FIGS. 1 and 2 illustrate drive 28 provided to move the mask 10 and detector 8 with respect to the subject 6 but this drive need only be capable of motion over very small distances, corresponding to order one pixel. Note that in FIGS. 1 and 2 the drive 28 is arranged to move the stage 4 but it will be appreciated that equivalently it may be possible to drive the movement of mask 10 and detector 8 using one or more drives instead.

Alternative Arrangements

As well as the motion in the x direction, the arrangement described may be combined with a helical acquisition scheme in which as well as rotation about the y axis there is also linear motion about the y axis. Thus, in this arrangement a sequence of images is captured at different rotation angles θ, with small linear motions in the x direction as discussed above but additionally an increment in the y direction for each new image in the sequence. Such helical acquisition schemes are well known in the art and will not be described further.

In contrast to the apparatus shown in FIG. 1 and FIG. 2 in which the beamlets are long, thin blades of radiation that extend uniformly in the y-direction (into the paper), other system geometries are possible. For example, the setup could be seen from the side, where the beamlets are laminar and extend uniformly into the plane of the paper.

The above examples all use a mask 10 that has structure in the x direction but which simply has long slits in the y direction. It is also possible to use a mask 10 with structure in both the x and the y direction, i.e. an array of apertures instead of an array of elongated slits.

In an alternative arrangement, the detector 8 is a one dimensional detector, not a two dimensional detector, with structure only in the x direction. In this case, a plurality of one dimensional images are captured and the resulting CT image is a two dimensional CT image. Translation of the subject or the imaging system along Z may be used to enable the reconstruction of a 3D volume.

In a particular arrangement, the apertures of the mask 10 are a series of square or round mask apertures in a two dimensional array, structuring the beam into an array of pencil beamlets. Such an alternative geometry leads to the presence of higher spatial frequencies than the cut-off normally dictated by the source and detector blur along other than the in-slice direction (x-z plane), provided that the mask adheres to a specific geometrical design. In essence, the aperturing along the respective direction must be smaller than the combined detector and source blur along that direction, and the individual beamlets must be spaced apart sufficiently such that they remain sufficiently separated along that direction.

Note that when using a mask 10 structured in the y direction the movement of the mask 10 and detector 8 should include motion in the y direction with respect to the subject, for example by using a helical or spiral acquisition scheme, to ensure that the sampling uniformity is increased also along y, in order to increase the spatial resolution along y.

Figure 3:
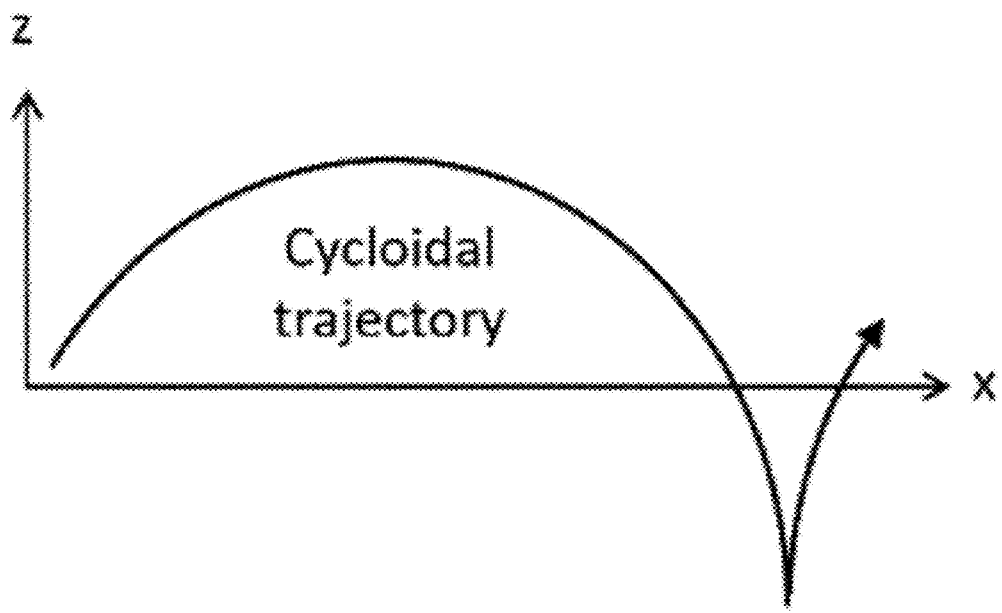
FIG. 3 illustrates the relative motion of a point within the sample and detector according to an embodiment of the invention in which the motion of individual sample points is rototranslational.

Instead of simultaneously rotating and translating, leading to the rototranslational motion illustrated in FIG. 3 and the collection of the data points as illustrated in FIGS. 5 to 8, it is also possible simply to rotate the sample as illustrated in FIG. 4. In this case, the use of an iterative reconstruction method rather than interpolation is preferred.

It is also possible to vary the set-up geometry of FIGS. 1 and 2 as long as acquisition schemes that take into account the potential multi-directionality of the available frequency content are used. In this case, instead of trying to select a value of d (FIG. 9) to cover the two-dimensional sinogram space as effectively as possible to allow for interpolation or alternative reproduction, it may instead be necessary to consider a 3D grid and to seek a uniform distribution of datapoints across a 3D grid.

In this case, the sample may be translated in both the orthogonal directions (x and y) at the same time as being rotated to capture suitable data.

Adding an array of beam stops in the form of mask 30 in front of the detector ("edge illumination" setup) is not the only way of switching from attenuation into phase contrast mode. Equivalently, one can use an "inter-pixel illumination" approach (Kallon et al., Journal of Physics D: Applied Physics 50, 415401, 2017) or a "beam tracking" approach (Vittoria et al., Applied Physics Letters 106, 224102, 2015); none of these methods relies on the use of beam stops. In the first method, each beamlet is aligned with the border of two adjacent detector pixels, and the beamlets' change of direction due to refraction is retrieved by comparing the intensities recorded in these adjacent pixels before and after the sample has been inserted in the setup. In the second method, a high-resolution detector is used to resolve each individual beamlet and to physically track their refraction by comparing beam profiles acquired before and after the insertion of the sample.

Although the embodiments described above have the mask on the source side of the sample, to reduce dose, in applications where dose is not important, for example when imaging inorganic samples, the mask can be located on the opposite side of the sample to the X-ray source. In this case, the beamlets created by the mask still define regions of the sample when projected back through the mask and the same high resolution can be obtained.

The above discussions focus on reconstruction of unmeasured values in the sinogram by interpolation. However, this is not the only approach. In the alternative, it is possible to use an iterative reconstruction scheme for directly reconstructing a representation of the sample without the need to first estimate any unmeasured values by interpolation.

Let us consider a single slice of the sample in the y direction for a given rotation angle θ. This slice can be described by the function $O_\theta(x, z)$. The projection image P, acquired with the described system is obtained from the following equation: $P(x, \theta) = M(x, \theta) \int O_\theta(x, z) dz$, where M describes the modulation imposed by the mask. For an ideal mask, $M(x, \theta)$ is equal to 1 at the positions of the apertures, and equal to 0 at the absorbing septa. The measured sinogram can therefore be written as $P(x, \theta) = M(x, \theta) \mathcal{R}[O](x, \theta) = \mathcal{R}_M[O](x, \theta)$, where $\mathcal{R}[O]$ indicates the Radon transform of the sample function O, and $\mathcal{R}_M$ indicates the joint operation of the Radon transform and mask modulation. $\mathcal{R}_M$ is a linear operator which describes the image formation process, and the problem of reconstructing O, from the knowledge of the sinogram P, can be solved through several iterative algorithm for linear problems.

One possibility is to use a gradient descent approach to solve the linear system in the sense of linear least squares. Let us assume that $O_n$ is the reconstructed slice of the sample after n iterations of the algorithm. We have that $P_n = \mathcal{R}[O_n]$, and $\Delta P_n = P - P_n$ is the residual error between the reconstructed and measured sinograms. The sample function can be updated using the following equation $O_{n+1} = O_n + \alpha \mathcal{R}^*_M[\Delta P_n]$, where α is a constant which determines the weight of the update term, and * indicates the adjoint operator. Note that $\mathcal{R}^*_M[\Delta P_n] = \mathcal{R}^*[M \Delta P_n]$, and $\mathcal{R}^*$ is the backprojection operator. An initial guess of the sample function $O_0$ is needed for the algorithm, and this can be the reconstruction obtained from the 2D interpolation of the missing data, or simply a zero matrix.

Thus, in this way it is possible to directly reconstruct the image without requiring the missing data points to be interpolated first. A regularisation term could also be added to improve image quality in the final reconstruction.

Results

We present below images captured using a method and apparatus according to the invention.

Figure 10:
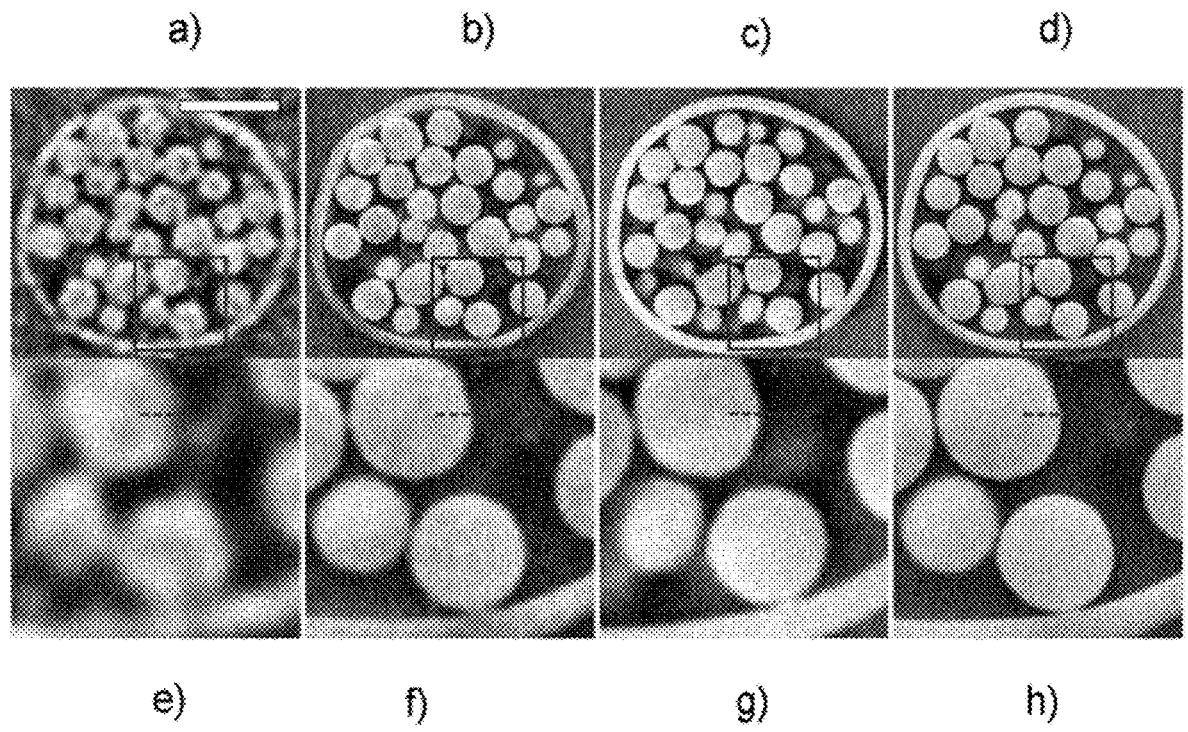
FIGS. 10 (a) and (e) illustrate an image according to a comparative example and FIG. 10 (b), (c), (d), (f), (g) and (h) illustrate an image taken with methods and apparatus according to the invention.
Figure 11:
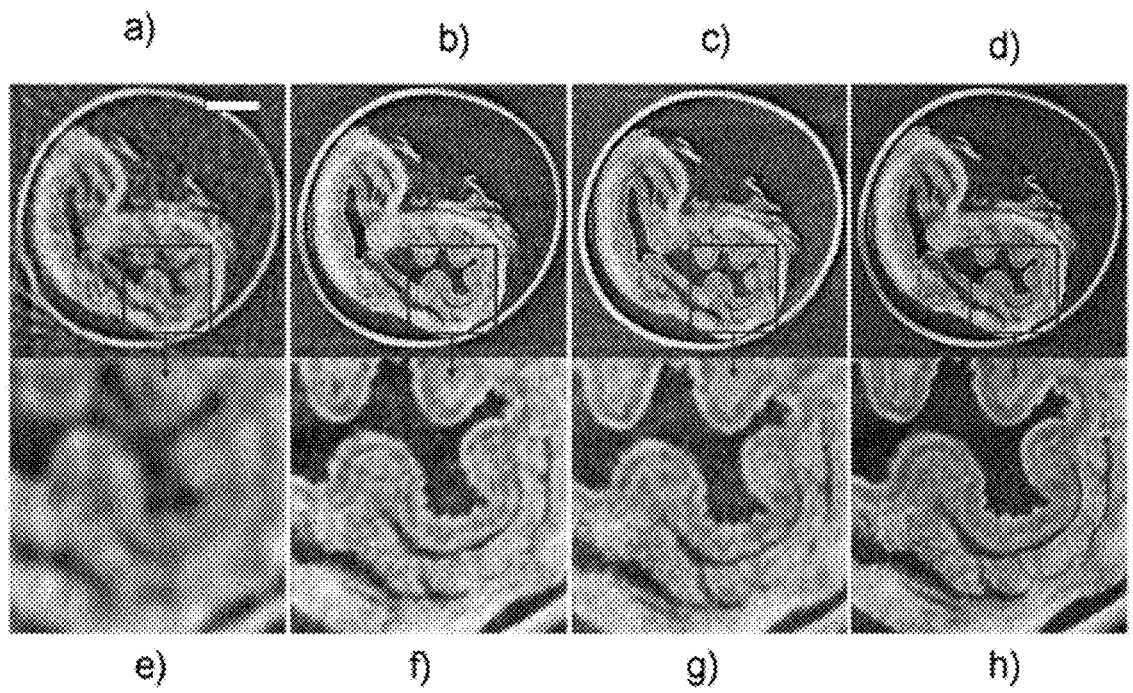
FIGS. 11 (a) and (e) illustrate an image according to a comparative example and FIG. 10 (b), (c), (d), (f), (g) and (h) illustrate an image taken with methods and apparatus according to the invention.

FIGS. 10 and 11 show tomograms of a sphere phantom and a biological specimen (a rabbit esophagus) which have been obtained using a method according to the invention using an interpolation scheme. To increase the contrast-to-noise ratio for these weakly attenuating samples, data were acquired in phase contrast mode as illustrated in FIG. 2. Note that FIGS. 10 and 11 show a section through the three dimensional image captured by the CT method and apparatus. Sub-images (e) to (h) are zoomed parts of the image shown in (a) to (d) respectively.

Although the computed tomography technique captures three-dimensional images, these cannot be presented as two dimensional figures and so FIGS. 10 to 13 are in fact sections of a plane through the complete CT image.

The images according to methods according to the invention are the images in (b) and (c) and the zoomed data in (f) and (g). To create these images, an interpolation scheme was used to reconstruct a three dimensional image from the sampled data points (the filled circles in FIGS. 4 to 8). In particular, a 2D cubic interpolation scheme was used taking as the inputs the sampled (filled) points and using these to interpolate the values of the remainder of the data points. The mask used in the experiments had a period of approximately 80 μm and an aperture width of 10 μm, matching the values assumed in FIG. 9. The sample translation per angular increment applied during rototranslational sampling was d=0.25p, corresponding to the grid pattern illustrated in FIG. 6 and to a value that is in close proximity to one of the local maxima of the grid quality indicator plotted in FIG. 9.

Figure 6:
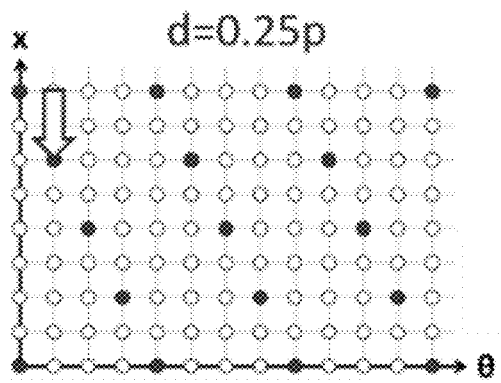

Thus, datapoints corresponding to the filled circles in FIG. 6 were measured and the values for the open circles were calculated by interpolation. The complete set of values (filled and unfilled circles) was then simply fed into a conventional image reconstruction algorithm.

The tomograms shown in panels (a) and (e) of FIGS. 10 and 11 are comparative examples acquired without the rototranslational scheme, i.e. without translation and with d=0. In this case, the distribution of the available datapoints does not allow translating the high spatial frequencies introduced by the sub-pixel beam fractioning into an increased spatial resolution in the reconstructed slices when applying interpolation before reconstruction.

The other comparative examples are panels (d) and (h) of FIGS. 10 and 11; the tomograms shown here were reconstructed after acquiring additional datapoints by dithering, by which the sample is translated laterally in multiple steps smaller than the mask period at each rotation angle, a frame is acquired at each step, and all frames are subsequently recombined into an up-sampled projection. Note that dithering is a significantly different procedure to rototranslational sampling; although both involve a lateral translation of the sample, the former requires a full sample scan at each rotation angle, while in the latter the sample is shifted by one step only (by a fraction of the total dithering distance i.e. the sum of all the dithering steps) for each rotational increment; such lateral translation can also be performed continuously i.e. "step" should be interpreted generally. Since dithering reduces the lateral sampling interval (making it a much closer match to the sampling needs of the high spatial frequencies made accessible through the use of beamlets), the resulting tomograms feature a better spatial resolution albeit at a significantly increased dose (by a factor of eight in this case, as this was the number of scanning steps necessary to ensure the entirety of the sample gets "seen" by the beamlets), which is completely avoided by the rototranslational scheme.

Note that panels (b), (c), (f) and (g) of FIGS. 10 and 11 tomograms acquired with the rototranslational scheme. Here, the number of datapoints (and therefore the delivered dose) was the same as in panels (a) and (e), in contrast to panels (d) and (h) which used eight times the dose.

Panels (b) and (f) in FIGS. 10 and 11 were acquired in a step-and-shoot manner, in which the sample was kept in a fixed position during the collection of each frame, and both the sample rotation and translation were carried out during detector read-out.

Panels (c) and (g) were acquired continuously, during which both rotation and translation were performed without interruption. Such a continuous acquisition has the advantage that scans can be fast, as dead time caused by stop-starting the motors are eliminated.

By comparing these results in panels (b), (c), (g) and (g) to panels (a) and (e), it is apparent that rototranslational sampling leads to a significant spatial resolution increase, on a level comparable to the high-dose reference data. Indeed, the results in (b) and (c) are surprisingly close to those illustrated in panels (d) and (h) which were captured using eight times as much radiation dose.

This shows the utility of the proposed approach in obtaining useful high quality CT images at a relatively low dose.

The resolutions of the images in FIGS. 10 and 11 were calculated to provide a quantitative figure for each of these approaches.

To do this, an error function was fitted to the profiles to increase accuracy, line spread functions were calculated via differentiation, and their full width half maxima (FWHM) were extracted and considered a measure of spatial resolution.

Without rototranslational sampling, i.e. in image (a) the spatial resolution was 90 µm. The images in (b) and (c) gave resolutions of 27 µm and 32 µm. The high resolution image (d) gave a resolution of 14 µm. The slightly worse performance of the continuous rototranslational acquisition compared to the step-and-shoot one can be explained by the fact that the uninterrupted sample motion introduces an additional level of blur. Thus, the method according to the invention (b) and (c) gave rise to much better resolutions than that of the comparative example (a) at a much lower dose (a factor eight less) than the high resolution example (d).

These quantitative results are confirmed by the qualitative observations in the zoomed-in regions displayed in panels (e)-(h) of FIG. 11, showing sections of the imaged rabbit esophagus. This specimen originates from research into whole organ decellurisation methods for tissue engineering applications. An indicator for the performance of such methods is the ability to preserve the specimen's microstructural integrity. Panel (h) provides a sufficiently high spatial resolution to identify major anatomical structures in the esophagus, as indicated by the arrows (1. mucosa, 2. sub-mucosa, 3. muscularis propria, 4. adventitia). However, this information is almost entirely lost in panel (e), where neither dithering nor rototranslational sampling was applied. As shown in panels (f) and (g), switching to rototranslational sampling restores the spatial resolution to a sufficient extent to allow an effective assessment of the anatomical structures without requiring any increase of either the delivered dose or exposure time.

The above example uses interpolation to reconstruct the additional, non-measured datapoints (empty circles).

Figure 12:
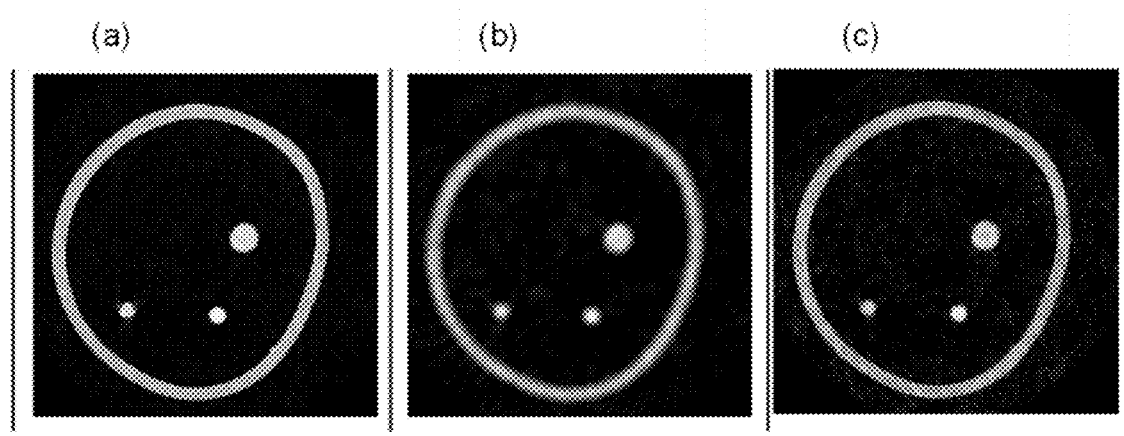
FIG. 12 illustrate images related to an alternative method.

As an alternative, an iterative reconstruction method can be used to construct a 3D image without the intermediate step of interpolating to find additional datapoints in the sinogram array, which also gives good results as will be illustrated in FIG. 12.

FIG. 12(a) illustrates a high resolution image taken with a high dose, using dithering. The upper image is the captured image which has a resolution (Full width at half maximum, FWHM) of 13 µm.

FIG. 12(b) is a comparative example made without using the method according to the invention at the same dose as FIG. 12(c) showing a worse image and a resolution of 72 µm.

FIG. 12(c) shows an image using a method according to the invention. Unlike the examples presented in FIGS. 10 and 11, the image in FIG. 12(c) was obtained using an iterative approach to directly calculate the image without first interpolating. It will be seen that the approach gives an image approaching the high resolution image of FIG. 12(a) but with ten times lower dose. The resolution was calculated to be 18 µm. Thus the use of the iterative approach can also give very good results.

Figure 13:
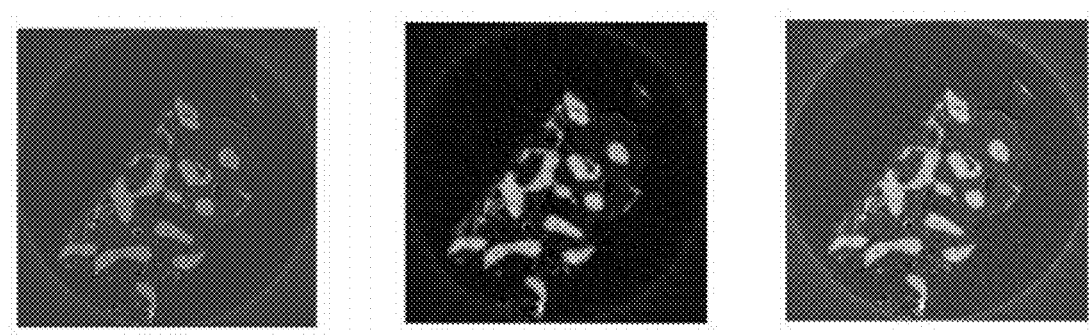
FIG. 13 illustrates images related to comparative examples and an alternative method.
Figure 14A:
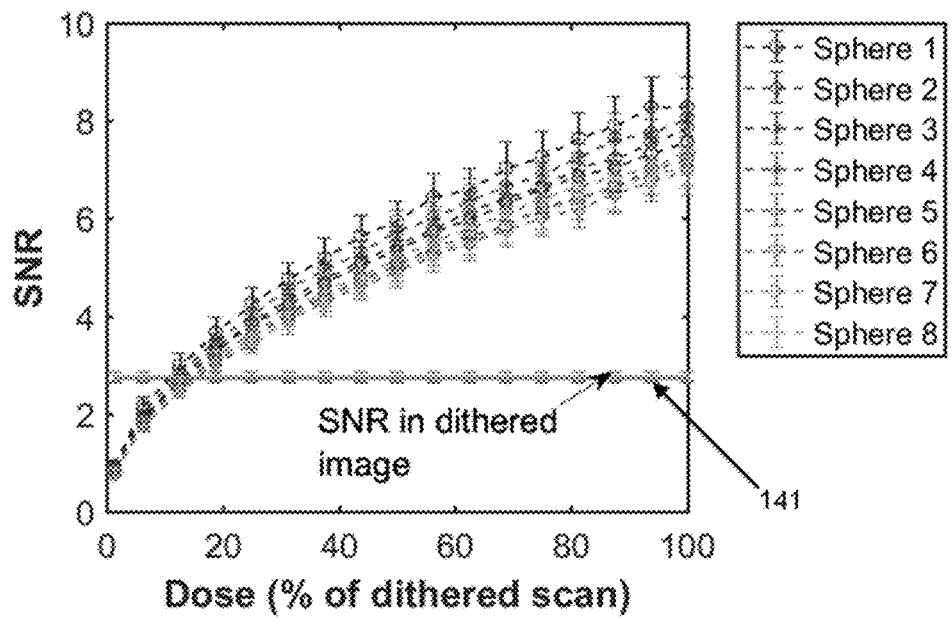
FIGS. 14 (a) to (i) show signal-to-noise values as a function of dose, for CT images obtained from simulated data.
Figure 14B:
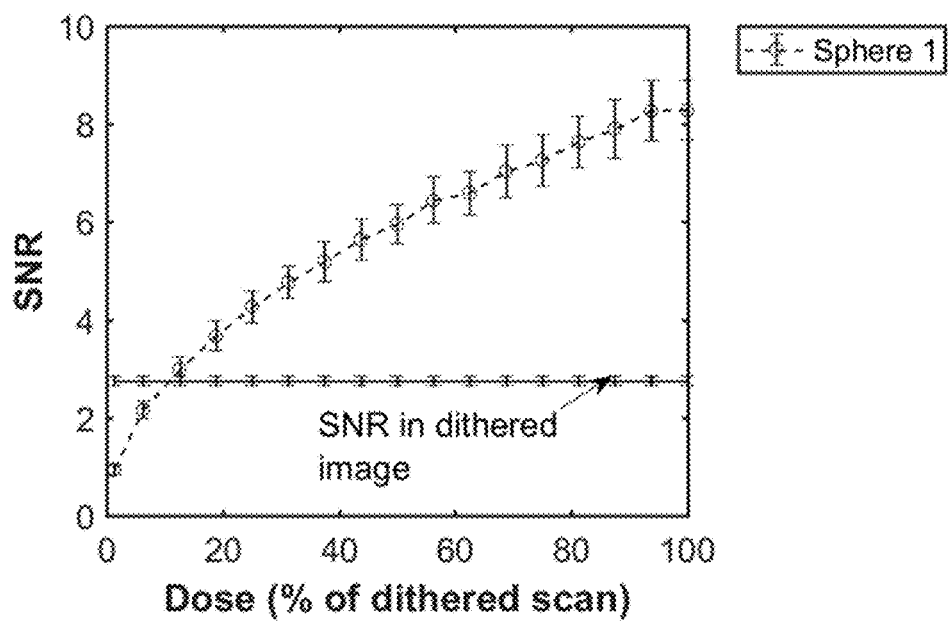
Figure 14C:
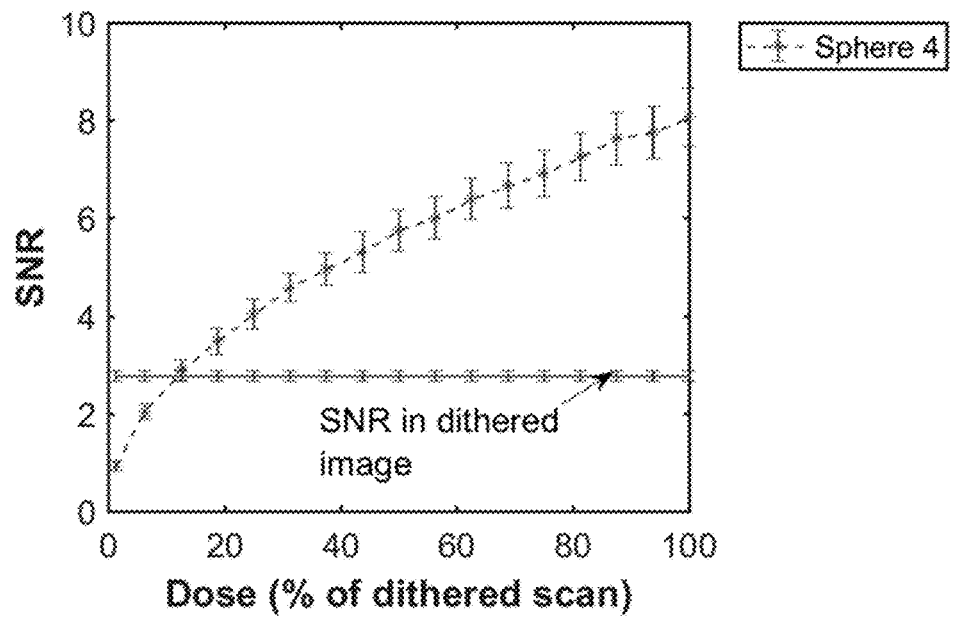
Figure 14D:
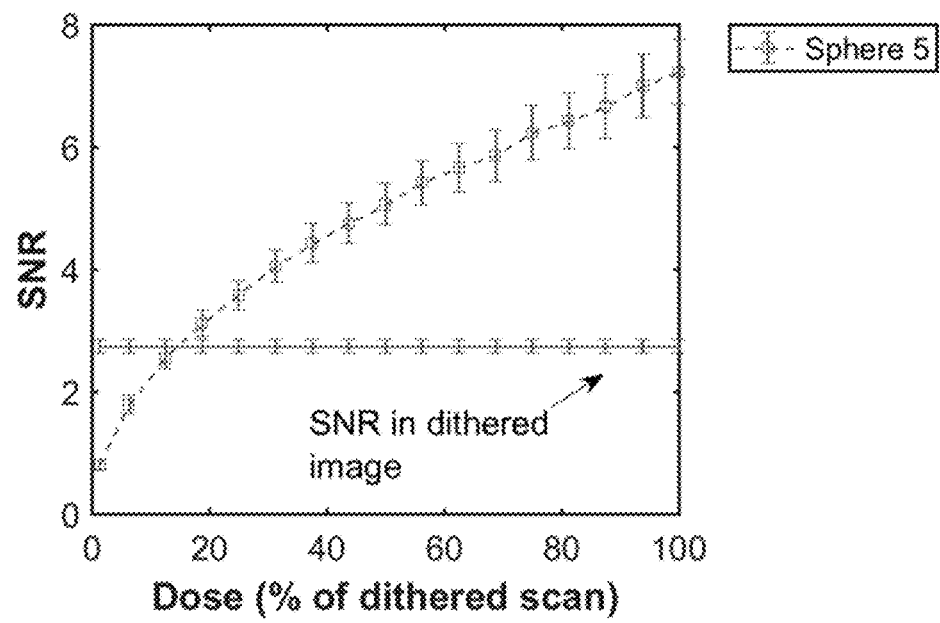
Figure 14E:
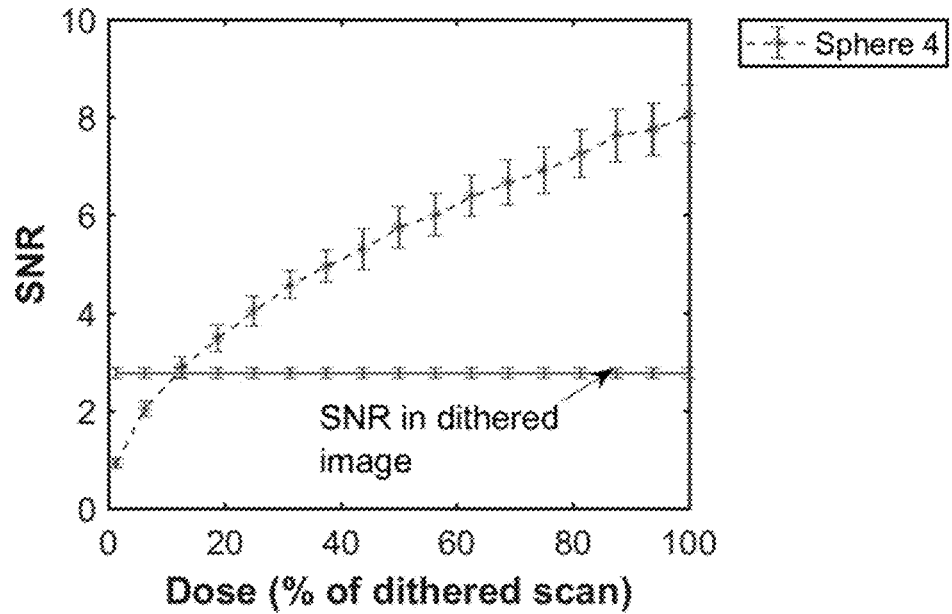
Figure 14F:
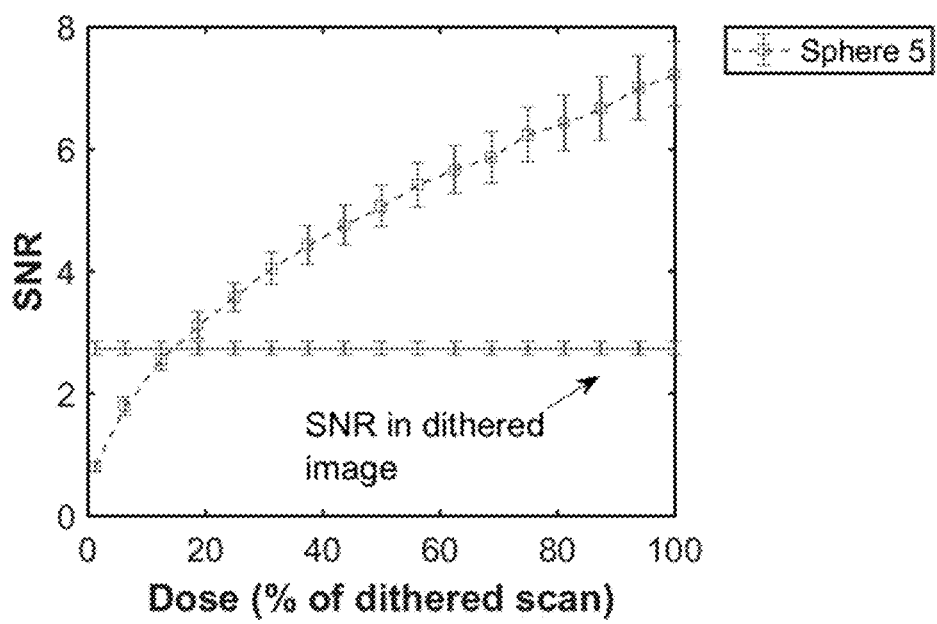
Figure 14G:
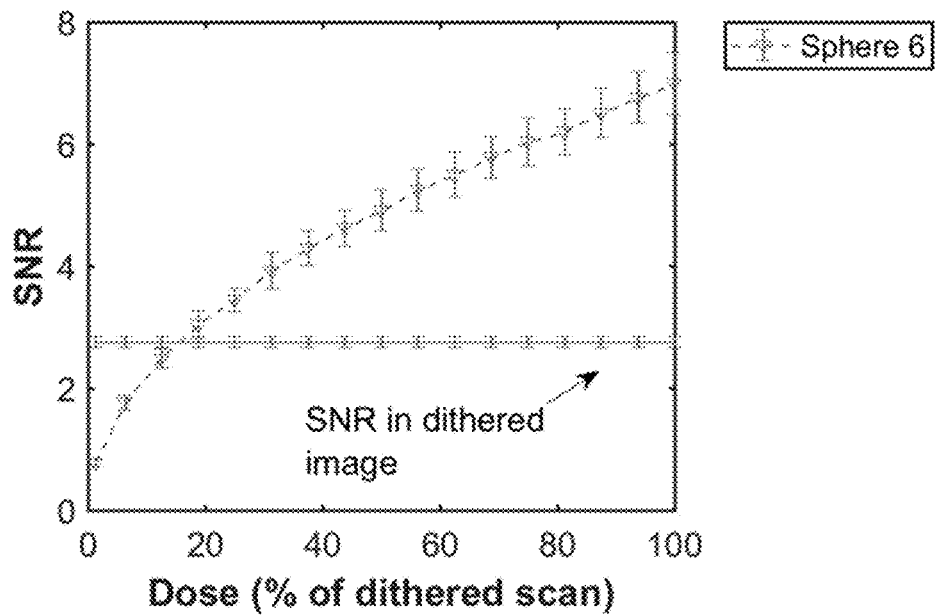
Figure 14H:
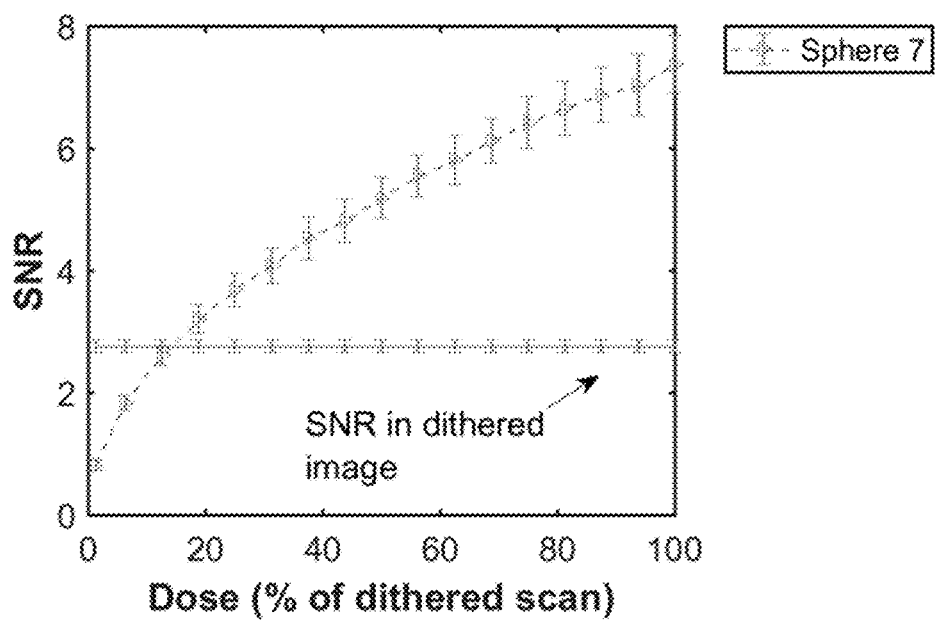
Figure 14I:
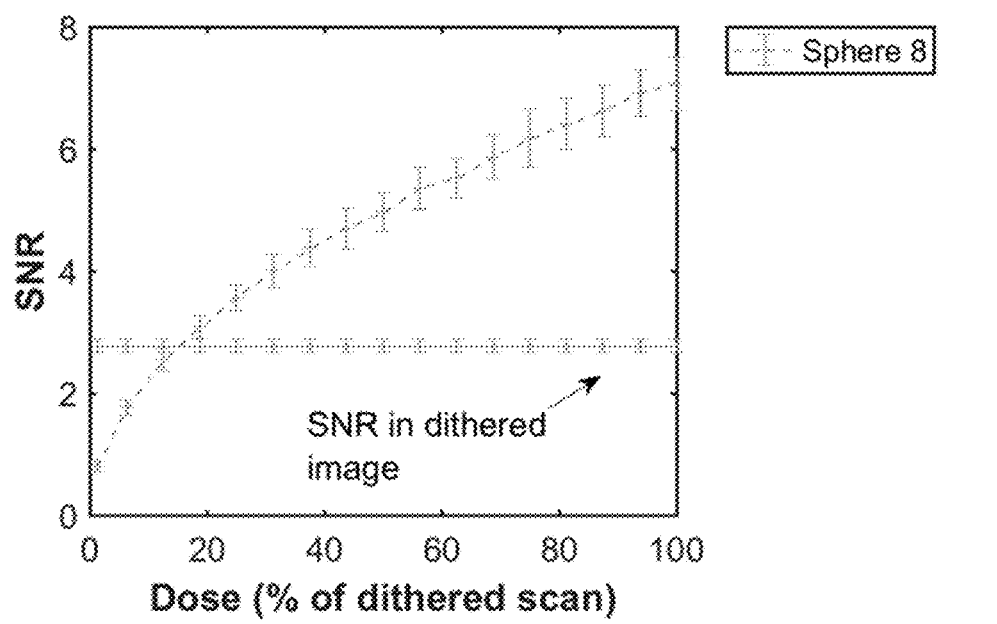

FIG. 13 illustrates a small bone splinter imaged in three ways. FIG. 13 (a) is a high resolution image imaged in the same way as FIG. 12(a) i.e. taken with a high dose with dithering as a comparative example.

FIG. 13 (b) illustrates sample scanned in another comparative example. In this case, a mask is used with rotation but no translation, corresponding to the arrangement illustrated in FIG. 4. The resolution is significantly reduced compared with FIG. 13(a). In this case, the reconstruction is to a resolution corresponding to the mask pitch.

FIG. 13(c) illustrates a sample scanned in accordance with the invention, again with rotation and no translation and hence also corresponding to the arrangement in FIG. 4. In this case, an iterative reconstruction algorithm is used that reconstructs a 3D representation of the sample at a finer mask pitch that the pixel resolution. Exactly the same number of images were captured as in FIG. 13(b)—the difference is the finer grain of the iterative reconstruction algorithm used.

It will be seen that the reconstructed image of FIG. 13(c) gives better resolution than the image in FIG. 13(b), though not as good as the image in FIG. 13(a). Thus, even without using translation in the x direction additionally to the rotation around the y axis, the presence of the mask makes it possible to capture structure at a higher resolution than F.

It will be appreciated that this approach has some advantages in that it is not necessary to move the subject 6, and hence there is no need for a drive 28 to move the subject by small amounts. This can be useful in some applications.

As discussed above, in some preferred embodiments, the computed tomography method is carried out using rototranslational sampling. With the rototranslational sampling approach, the lateral translation step involves a single translation step for each rotational increment. By comparison, obtaining data by dithering involves multiple translations for each rotational increment.

The dose saving capabilities of the rototranslation approach can be demonstrated by comparing data obtained by this approach to data obtained by dithering.

Figure 16A:
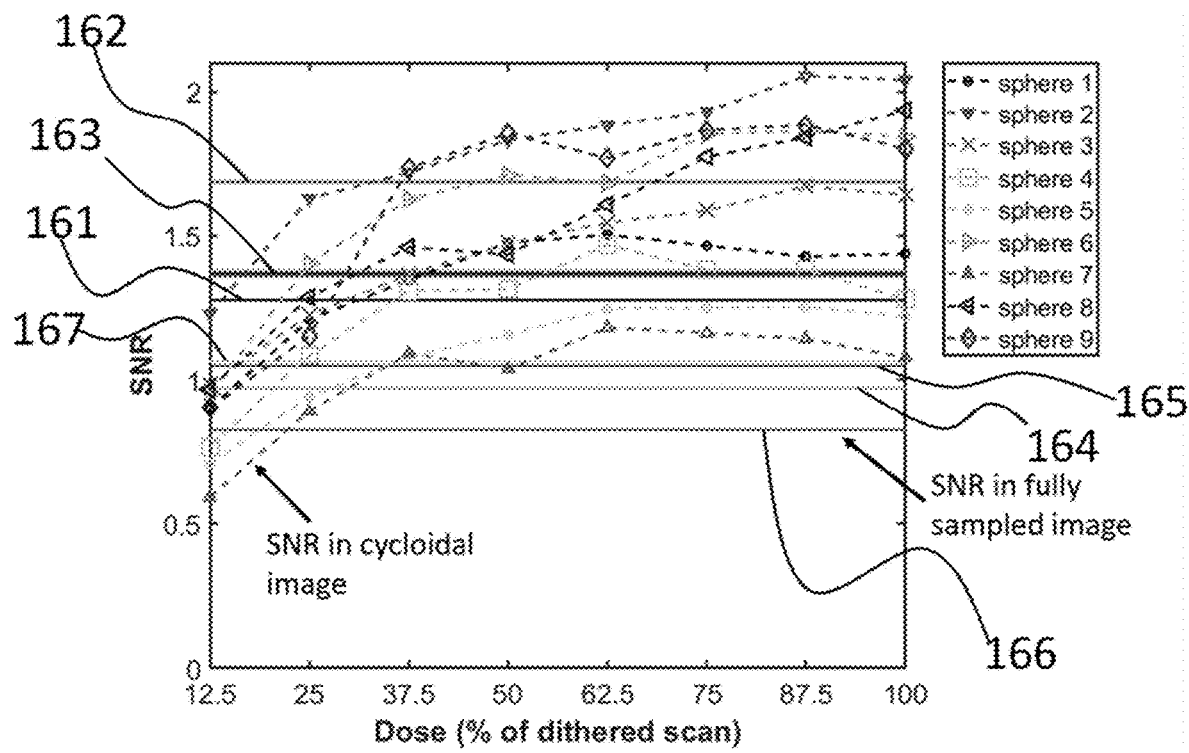
FIG. 16 (a) shows signal-to-noise values as a function of dose, for CT images obtained from experimental data.

FIGS. 14a-i and 16a show signal-to-noise ratio (SNR) values for tomograms obtained from simulated and experimental scans, respectively. FIGS. 14a-i show SNR values obtained from simulated scans of a numerical test phantom. FIG. 16a shows SNR values obtained from an experimental scan of a real test phantom. The samples comprised of several polyethylene spheres in a plastic cylinder.

Referring to FIGS. 14a-i, a single scan of the numerical sample was simulated using dithering. The dose used for this scan is taken as the reference dose (i.e. 100% dose). Multiple scans were simulated using rototranslational sampling, each scan at a different dose, up to a dose matching that of the fully sampled data (i.e. up to 100% of reference dose). The tomograms obtained from the scans were analysed in terms of their SNR, and the results plotted.

Referring to FIGS. 14a-i, the SNR values for a tomogram obtained by simulating a scan using dithering are compared to SNR values obtained by simulating scans using rototranslational sampling. The sample translation distance per angular increment (d) was d=0.25p. The tomograms obtained from the simulated data were obtained in attenuation contrast mode. The tomograms were reconstructed by applying bivariate interpolation to the sinograms, followed by a standard tomographic reconstruction algorithm.

Seventeen different rototranslational scans were simulated, each having a different dose, and a corresponding tomogram was generated for each scan. The SNR values for 5 spheres in the numerical phantom are plotted as a function of dose in FIG. 14a. Horizontal lines 141 represent the SNR values for the respective spheres in the tomograms obtained by dithering.

For each tomogram obtained by a rototranslational scan, SNR was measured inside each sphere in the numerical phantom by defining a region-of-interest (ROI) away from the sphere boundary and extracting the signal as the average grey value and the noise as the grey value standard deviation in that ROI. The measured SNR was then plotted against the dose (expressed as a percentage of the dose in the fully sampled data).

The SNR values for each sphere have also been plotted separately in FIGS. 14b-14i.

It can be seen that the SNR in the simulated computed tomography images obtained using rototranslational sampling increases with dose for all spheres. Moreover, an SNR comparable to that obtained using dithering is achieved at a much lower dose. Notably, it is achieved already at approximately 15-20% of the reference dose (some variability can be seen for the different spheres).

Figure 15:
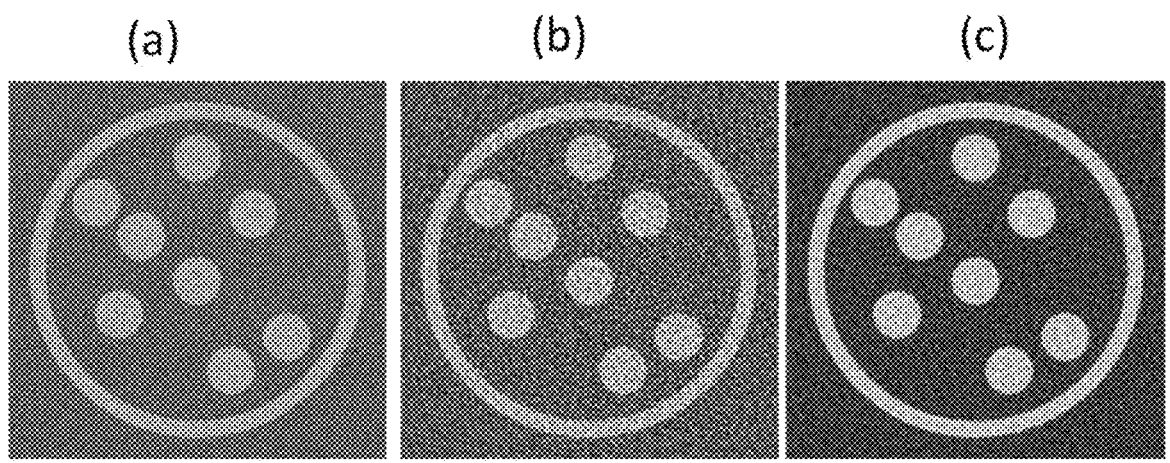
FIG. 15 shows CT images obtained from simulated data.

FIG. 15 shows some computed tomography images of the sample, obtained from simulated data. FIG. 15a is a tomographic image obtained by using dithering. The dose used to obtain the dithered image is considered the reference dose (100% dose).

FIG. 15b shows a computed tomography image, obtained by simulating a scan carried out using rototranslational sampling. This image was obtained with approximately 19% of the reference dose. FIG. 15b has a comparable SNR to that obtained for FIG. 15b, but with only approximately 19% of the dose.

FIG. 15c shows a simulated computed tomography image, which was obtained by simulating a scan carried out using rototranslational sampling. This image was obtained using the same dose as the dithered image (i.e. 100%). The image in FIG. 15c provides a much higher SNR (more than twice as high) than the images of FIG. 15a or FIG. 15b.

A single experimental scan of the real phantom was carried out using dithering, and multiple frames were acquired at each dithering position. A dithered image was reconstructed from only one frame acquired at each dithering position; the dose used for this image is taken as the reference dose (i.e. 100% dose). Eight scans using rototranslation sampling were mimicked by subsampling the dithered, multi-frame data in such a way that only those dithering positions corresponding to rototranslation sampling were considered. Eight tomograms were reconstructed from an increasing number of frames (ranging from one to eight frames) per dithering position. Hence, the tomograms were effectively obtained from between 12.5% to 100% of the reference dose. The tomograms obtained in this way were analysed in terms of their SNR, and the results plotted.

FIG. 16a shows a plot of SNR as a function of dose, for tomograms obtained experimentally mimicking rototranslational sampling with a sample translation distance (d) per angular increment of d=0.5p. The tomograms were obtained in phase contrast mode. The tomograms were reconstructed by applying bivariate interpolation to the sinograms, followed by a standard tomographic reconstruction algorithm. Again, for each tomogram, an SNR value was calculated for a number of spheres in the sample.

FIG. 16a also shows the SNR values for a tomogram obtained by dithering. Horizontal lines 161-167 represent the SNR value for the spheres in the tomogram obtained by dithering. Line 161 indicates the SNR value for sphere 1. Line 162 represents the SNR value for sphere 2. Line 163 represents the SNR value for spheres 3, 6 and 8. Line 164 represents the SNR value for sphere 4. Line 165 represents the SNR value for sphere 5. Line 166 represents the SNR value for sphere 7. Line 167 represents the SNR value for sphere 9. It can be seen from FIG. 16a that SNR in the tomograms obtained by rototranslational sampling also increases with dose for all spheres, and that an SNR comparable to that in the corresponding sphere in the fully sampled image is achieved already at a much lower dose, thereby supporting the simulated results.

The dose saving capability is also apparent in the experimental case, since in the experimental data a comparable SNR is achieved with 15-40% of the dose of the fully dithered scan.

Figures 16B, 16C, 16D:
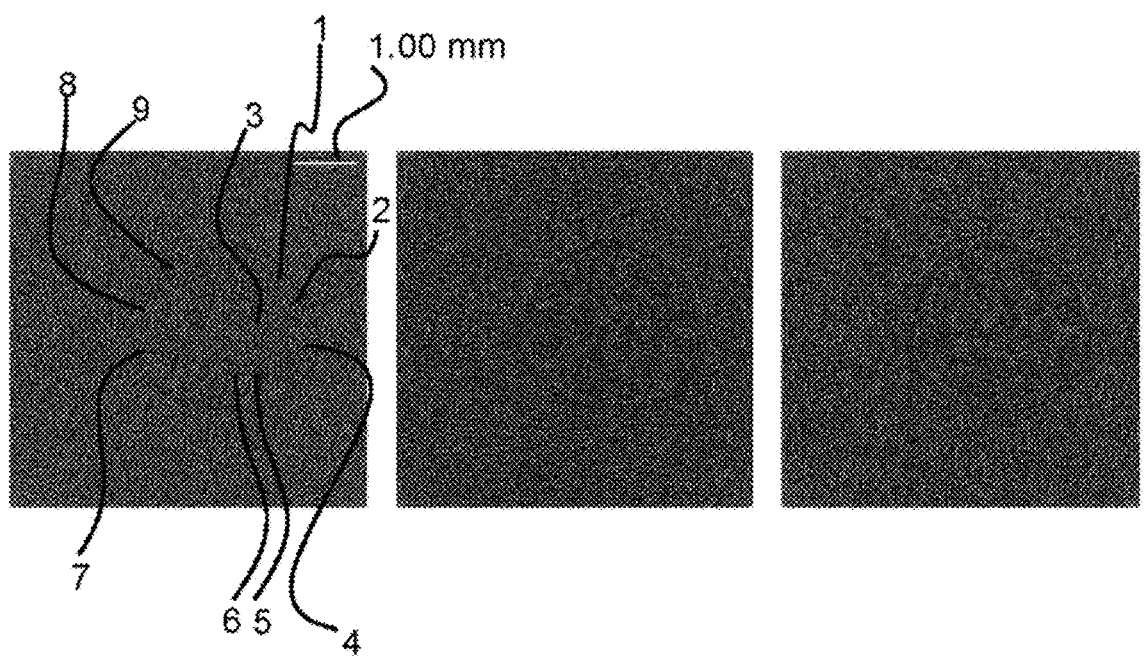

Some of the images used to calculate SNR values in FIG. 16a are shown in FIGS. 16b, 16c and 16d. FIG. 16b shows a fully sampled image. FIGS. 16c and 16d show two of the tomograms obtained by rototranslational sampling used in FIG. 16a. FIG. 16c is an image obtained at 25% of the dose (exhibiting a comparable SNR for several spheres) and FIG. 16d is an image obtained at 100% of the dose (exhibiting a greater SNR throughout), respectively.

Note that the experimental images are of a different visual appearance than the simulated ones. This is because the experimental data were acquired in phase contrast mode, while the simulated data were obtained in attenuation-contrast mode (cycloidal computed tomography is compatible with both contrast modes). Phase contrast is responsible for the bright and dark fringes at the borders of the spheres and the cylinder. However, away from the boundaries the signal is effectively only due to attenuation, hence in the ROIs in which the SNR is measured the experimental and simulated images show the same source of contrast, making a comparison between both appropriate.

The invention claimed is:

1. A computed tomography method, comprising:
generating an X-ray beam travelling in a beam direction z from an X-ray source having a focal spot;
using a mask having a plurality of block regions and a plurality of apertures having a period p in a first orthogonal direction x, orthogonal to the beam direction z to divide the beam into a plurality of X-ray beamlets;
passing the X-ray beam through a subject;
capturing an image on an X-ray detector having an array of pixels extending in the x direction, the plurality of pixels having a period a in the x direction;
moving the subject with respect to an imaging system comprising the X-ray source, mask and the X-ray detector;
capturing a plurality of images as the subject is moved with respect to the imaging system, each image corresponding to a rotation angle θ and being in a form of a plurality of measured datapoints as a function of x, and storing the measured datapoints; and
reconstructing a three-dimensional computed tomography image from the plurality of measured datapoints;
wherein the mask is structured such that each of the beamlets defines a region in the subject which when geometrically scaled to a detector mask is less than F, wherein F is a full width half maximum (FWHM) of an overall spread function caused by a combination of a finite size of the focal spot and a finite pixel resolution at a plane of the detector, in the x-direction; and the step of reconstructing reconstructs the three-dimensional computed tomography image at a finer pitch than the period p of the mask.

2. A method according to claim 1 wherein the mask is on an X-ray source side of the subject in the beam direction z so that the X-ray beamlets pass through the subject.

3. A method according to claim 1, wherein the step of moving the subject with respect to the imaging system comprises rotating around an axis in a second orthogonal direction y by the rotation angle θ, and translating in the first orthogonal direction x.

4. A method according to claim 1, wherein a density of measured datapoints in the x direction is a density of the plurality of pixels or less, and the measured datapoints are stored in a sinogram array having a density of elements in the x direction at least double the density of the plurality of pixels whereby the step of storing the measured datapoints in the sinogram array leaves at least half the datapoints as non-measured additional datapoints.

5. A method according to claim 4, wherein the step of reconstructing a computed tomography image comprises carrying out an interpolating step to obtain values of the sinogram array for the additional datapoints.

6. A method according to claim 4, wherein in the sinogram array the plurality of rotation angles θ are separated by Δθ and the plurality of values x corresponding to both measured and additional datapoints for a particular rotation angle θ are separated by Δx, wherein the translation of the subject between adjacent rotation angles separated by Δθ corresponds to nΔx, where n is a number selected to maximise a grid quality indicator describing how closely a grid of measured datapoints resembles a hexagonal grid.

7. A method according to claim 1, wherein the step of reconstructing a three-dimensional computed tomography image is carried out using an iterative reconstruction method.

8. A method according to claim 1, wherein p=a/m, where m is an effective magnification between the mask and the detector.

9. A method according to claim 1, further comprising capturing data in a helical pattern by translating the subject with respect to the imaging system additionally in a second orthogonal direction y perpendicular to the first orthogonal direction x.

10. A method according to claim 9 wherein the mask is structured to provide a two-dimensional array of beamlets in the x and y directions.

11. A method according to claim 1, wherein the captured images are phase contrast images.

12. A method according to claim 11 further comprising providing the detector mask in front of the X-ray detector, the detector mask comprising a plurality of apertures spaced apart in the first orthogonal direction and each beamlet overlapping one edge of a respective aperture in the first orthogonal direction.

13. A method according to claim 11 wherein the beamlets are aligned with regions between the pixels of the detector with each beamlet overlapping one edge of the regions in the first orthogonal direction.

14. A method according to claim 11 wherein a density of pixels in the x direction is higher than a density of beamlets so that individual beamlets can be resolved by the X-ray detector.

15. A computed tomography apparatus, comprising:

an X-ray source for generating a beam travelling in a beam direction z from a focal spot;

a mask spaced from the X-ray source along the beam direction z having a plurality of block regions and a plurality of apertures having a period p in a first orthogonal direction x orthogonal to the beam direction z for dividing the beam into a plurality of X-ray beamlets;

a stage for supporting a subject in the beam;

a detector having an array of pixels having a period a in the x direction for capturing an image on an X-ray detector;

a drive for moving the stage with respect to an imaging system comprising the X-ray source, mask and the X-ray detector, including a rotation represented by a rotation angle θ; and a computer control means for controlling the drive to move the stage with respect to the mask and the detector and for capturing a plurality of images on the detector;

wherein the mask is structured such that each of the beamlets defines a region in the subject which when geometrically scaled to a detector mask is less than F, wherein F is a full width half maximum (FWHM) of an overall spread function caused by a combination of a finite size of the focal spot and a finite pixel resolution at a plane of the detector, in the x-direction.

16. A computed tomography apparatus according to claim 15, further comprising an image analysis computer for reconstructing a computed tomography image from the plurality of images;

wherein the computer control means is arranged to control the computed tomography apparatus to move the subject with respect to the imaging system.

17. The computer tomography apparatus according to claim 16, wherein moving the subject with respect to the imaging system further comprises rotating around an axis in a second orthogonal direction y by the rotation angle θ, and translating in the first orthogonal direction x.

18. The computer tomography apparatus according to claim 17, wherein the mask is structured to provide a two-dimensional array of beamlets in the x and y directions.

19. The computer tomography apparatus according to claim 17, wherein a density of measured datapoints in the x direction is a density of the plurality of pixels or less, and the measured datapoints are stored in a sinogram array having a density of elements in the x direction at least double the density of the plurality of pixels whereby the step of storing the measured datapoints in the sinogram array leaves at least half the datapoints as non-measured additional datapoints.

20. The computer tomography apparatus according to claim 15, wherein the mask is on an X-ray source side of the subject in the beam direction z so that the X-ray beamlets pass through the subject.

* * * * *